United States Patent [19]
Dabberdt et al.

[11] Patent Number: 5,553,508
[45] Date of Patent: Sep. 10, 1996

[54] PORTABLE INTELLIGENT WHOLE AIR SAMPLING SYSTEM

[75] Inventors: Walter F. Dabberdt; Kenneth D. Norris, both of Boulder; Steven R. Semmer, Westminster; Anthony C. Delany, Eldorado Springs; Jack R. Fox, Broomfield, all of Colo.

[73] Assignee: University Corporation For Atmospheric Research, Boulder, Colo.

[21] Appl. No.: 410,339

[22] Filed: Mar. 24, 1995

[51] Int. Cl.$^6$ .................................. G01N 1/26
[52] U.S. Cl. ........................ 73/63.02; 73/863.31
[58] Field of Search ................... 73/863.01, 863.02, 73/863.03, 863.31, 864.34, 864.62, 864.63, 31.05, 864.91, 865.51, 863.25

[56] References Cited

U.S. PATENT DOCUMENTS

| | | | |
|---|---|---|---|
| 3,540,261 | 11/1970 | Scoggins | 73/863.25 |
| 3,921,456 | 11/1975 | Newcomb, Jr. et al. | 73/863.02 |
| 4,116,067 | 9/1978 | Pankratz et al. | 73/863.31 |
| 4,458,544 | 7/1984 | Gyer et al. | 73/864.21 |
| 5,319,986 | 6/1994 | Padden et al. | 73/863.21 |
| 5,333,511 | 8/1994 | Boyum et al. | 73/863.01 |
| 5,404,763 | 4/1995 | Guggenheim | 73/863.31 |

*Primary Examiner*—Hezron E. Williams
*Assistant Examiner*—Nashmiya Ashraf
*Attorney, Agent, or Firm*—Duft, Graziano & Forest, P.C.

[57] ABSTRACT

The portable intelligent whole air sampling system performs in situ air sampling over multiple time periods at individually programmable times, rates and volumes. The system contains multiple independent disposable syringes that collectively provide a large sampling capacity for a large number of samples over an extended period. In addition, the unit/sampler features a battery powered system for portability, operational ability in a wide variety of environmental conditions, an internal time stamping feature to record time and date of events, and microprocessor controlled program features for flexible sampling options. The removable cassette/carousel provides sample portability to a sample extraction device that functions opposite the field sample intake device. Sampling system mechanical components include a removable syringe cassette/carousel, a motorized carousel drive, a motorized plunger extractor, and a motorized syringe selection fork. With the programmable microprocessor and three motor syringe selection and/or operation mechanisms, any number of syringes can be precisely operated during the sampling period by rotating a carousel to any available syringe. Sample extraction system mechanical components include a removable syringe cassette/carousel, motorized carousel drive, and motorized plunger depression drive. With a programmable microprocessor and two motor syringe selection and/or operation mechanism, the samples within any number of syringes can be precisely extracted. Further, varying sized carousels and varying sized disposable syringes can be combined for additional flexibility in the sampling or extraction system.

24 Claims, 9 Drawing Sheets

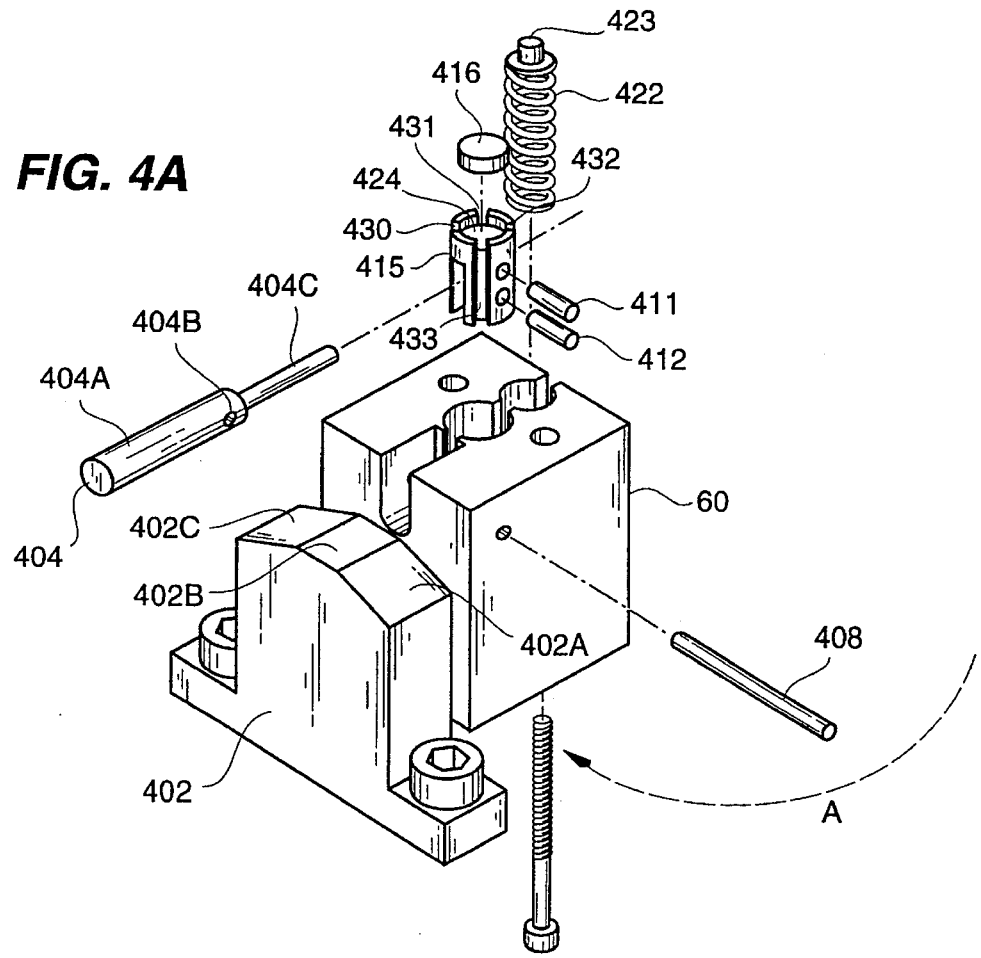
FIG. 4A
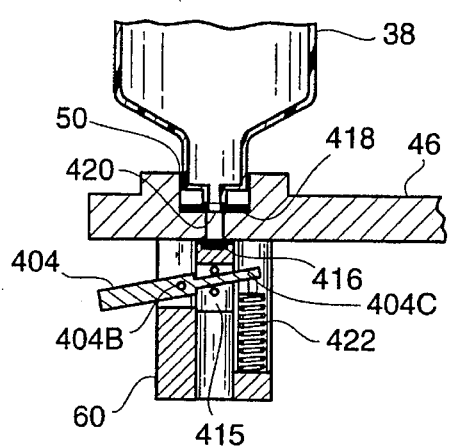
FIG. 4B
FIG. 4C

PORTABLE INTELLIGENT WHOLE AIR SAMPLING SYSTEM

GOVERNMENT FUNDED INVENTION

This invention was made with government support pursuant to Agreement Number ATM-8709659 awarded by the National Science Foundation. The United States Government has certain non-exclusive rights to this invention.

FIELD OF THE INVENTION

This invention relates to air sampling systems, and in particular, to a portable intelligent whole air sampling system for capturing ambient gases at or near the Earth's surface, for delivery to a laboratory without intervening contamination or dilution.

PROBLEM

It is a problem to provide a reliable, inexpensive, portable air sampling system that facilitates capturing air samples with high precision with respect to timing, rate, and volume of the sample obtained, and delivering the samples to a laboratory for analysis. Present sampling systems, whether air-borne, or ground-based, utilize devices including, but not limited to, large canisters, Tedlar bags, and carbon or chemically sensitive strips, among other types of air sampling collection systems. However, each of the above identified sampling systems is limited by the type of sampling container utilized, the programming capabilities, or the mechanical configuration on which the system is based. In particular, there is a great need to improve the sampling flexibility with respect to sampling periods, intervals, and volumes obtained.

Chemically sensitive strip systems provide highly specific air sampling data by exposing the chemically sensitive strips to ambient air. While this method provides precise information as to the presence of a particular chemical or chemicals, this system lacks the flexibility to capture a whole air sample for subsequent analysis to identify all chemicals contained in the air sample.

Tedlar bags provide the ability to capture high volume whole air samples in a lightweight flexible bag. While this system is typically used in ground-based and air-borne or tethered balloon-borne applications, it lacks flexibility in terms of a sampling period and a sampling interval. Instead, the system simply captures a fixed volume air sample at one time. In some Tedlar systems, a single bag has a simple inlet that is either opened or closed by a simple mechanical device, or oftentimes manually. In other Tedlar systems, a pump forces an air sample into the bag at a fixed rate. In either case, Tedlar bag systems provide limited control over the sampling rate and/or volume. Further, air-borne uses are subject to difficulty due to atmospheric pressure changes, wind, icing, extreme temperature, or any number of other factors that limit the precision of the rate and/or volume of a desired sampling.

Solid absorbent cartridges or hollow canisters are used in other systems, and provide the ability to capture large volume whole air samples for subsequent analysis. However, such systems are expensive, and provide limited sampling flexibility similar to Tedlar bags.

One improvement over single sample systems is the development of multiple Tedlar bag sampling systems. While such systems provide the flexibility to collect multiple individual samples, the systems are bulky and require individually dedicated mechanical apparatus including valves, ports, and air pumps, for each bag in the multiple bag system. In addition, problems exist regarding the rate and flow volume for each Tedlar bag as seen with single Tedlar bag systems.

For these reasons, it is desirable to have a portable intelligent air sampling system that is broadly programmable so multiple independent air samples can be captured with a wide variety of flexibility and minimal capturing apparatus. Specifically, it is desirable for the programmability to facilitate independent control of the sampling rate, periodic timing, and the sampling volume collected for each individual sampling container.

SOLUTION

The above described problems are solved and a technical advance achieved in the field by the portable intelligent whole air sampling system. While the present system can be adapted to air-borne or ground-based implementations by accommodating weight, size, materials, and power requirements, the following solution and detailed description focuses primarily on a ground-based embodiment.

The portable intelligent whole air sampling system facilitates multiple in situ air sampling each at individually programmable rates and volumes. The system contains multiple independent and disposable low-cost syringes that collectively provide a large sampling capacity over an extended period. Other features of the system include battery power portability, compatibility with a wide variety of environmental operating conditions, an internal time stamping feature to record time and date of events, and microprocessor controlled program features for flexible sampling options. Mechanical components include a removable cassette/carousel containing disposable syringes, a motorized carousel drive, a motorized plunger extractor, and a motorized plunger extraction fork. A programmable microprocessor controlling a three-motor syringe selection mechanism accommodates any number of syringes by rotating the carousel to any particular syringe and withdrawing the syringe plunger. In addition, the system is designed for low-cost, field maintainability, optional solar powering, and wire or wireless communications. The system also includes a laboratory sample extraction device requiring that only the removable carousel be transported between the field sampling site and the laboratory. Further, varying sized carousels and varying sized disposable syringes can be used in the system for additional flexibility as a matter of design choice. Details of the above described system are presented herein.

BRIEF DESCRIPTION OF THE DRAWINGS

FIG. 4A illustrates an exploded view of the air sample inlet/exhaust valve at the base of each sampling syringe;

FIGS. 4B and 4C illustrate cross-sectional views of an inlet/exhaust valve in a closed and open position respectively;

DETAILED DESCRIPTION

Figure 1:
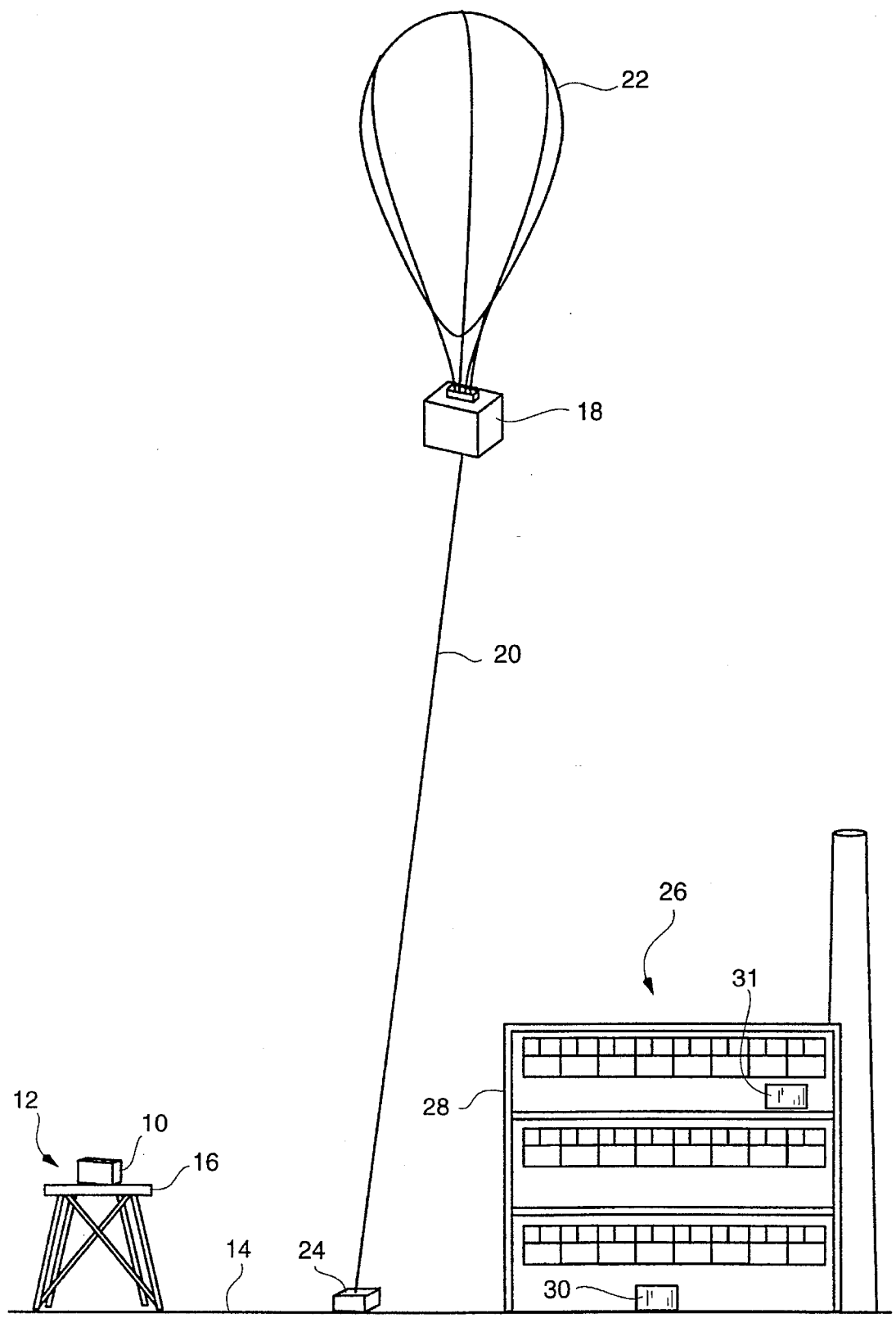
FIG. 1 illustrates ground-based, air-borne, and indoor settings for the portable intelligent air sampling system.

Sampling System Uses—FIG. 1

The portable intelligent air sampling system is fully contained within housing 10 as shown in the ground-based field setting 12 in FIG. 1. In the ground-based setting 12, the housing 10 can rest on a platform 16 or directly on the ground 14 as desired. In either case, the housing 10 is constructed of materials appropriate for a wide variety of environmental conditions so that the components internal to housing 10 are adequately protected. Alternatively, housing 10 can be partly sheltered from the elements with an independently supported overhead roof provided that ambient air can freely flow around housing 10 itself.

The portable intelligent air sampling system can alternatively be constructed of light weight materials so that housing 18, which is substantially similar to housing 10, can be lifted to low altitudes in a balloon-borne setting 20 by balloon 22 anchored to the ground 14 at anchor point 24. As with housing 10, housing 18 can be constructed with materials that protect the internal components of the sampling system from external elements.

The portable intelligent air sampling system may also be used in indoor settings 26, such as for example, a home, industrial, or manufacturing facility 28, where it is desirable to periodically monitor indoor air quality and/or content. Here, housings 30 and 31, being substantially similar to housing 10, are constructed of materials such that the sampling system can be placed anywhere in the facility 28 without subjecting components internal to housings 30 or 31 to harm.

Figure 2:
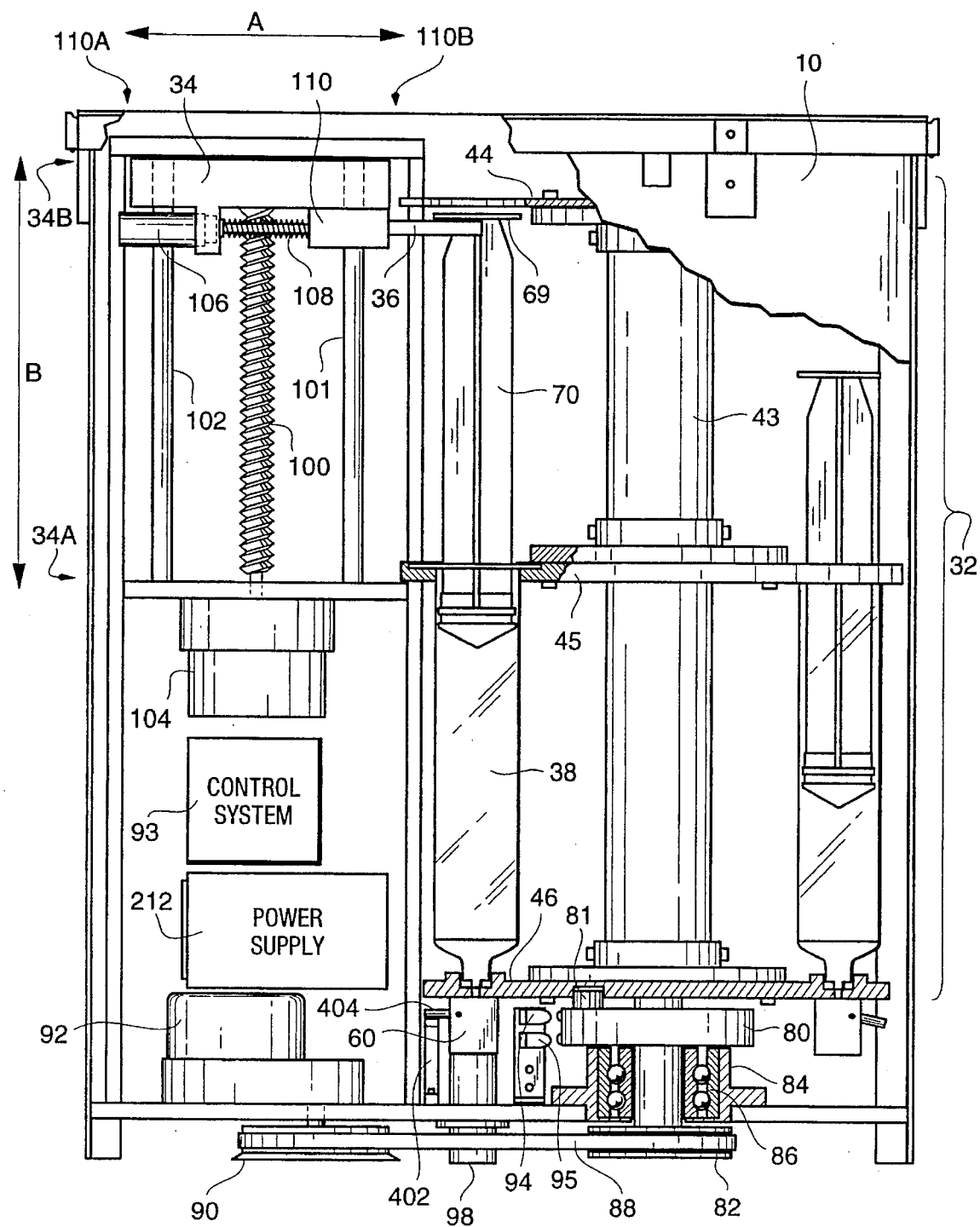
FIG. 2 illustrates internal mechanical components of the portable intelligent air sampling system.

Sample Capturing System Mechanical Components—FIG. 2

The internal mechanical components illustrated in FIG. 2 are fully contained within either of the housings 10, 18, 30 or 31, in any orientation as a matter of design choice. While the FIG. 2 illustration is oriented vertically, the system is equally functional in a horizontal orientation or any other orientation as a matter of design choice.

The primary mechanical components include, but are not limited to, a removable cassette/carousel 32, a plunger retractor 34, and a retraction fork 36. Each of these components and their collective interactions are described in turn below.

Figure 3:
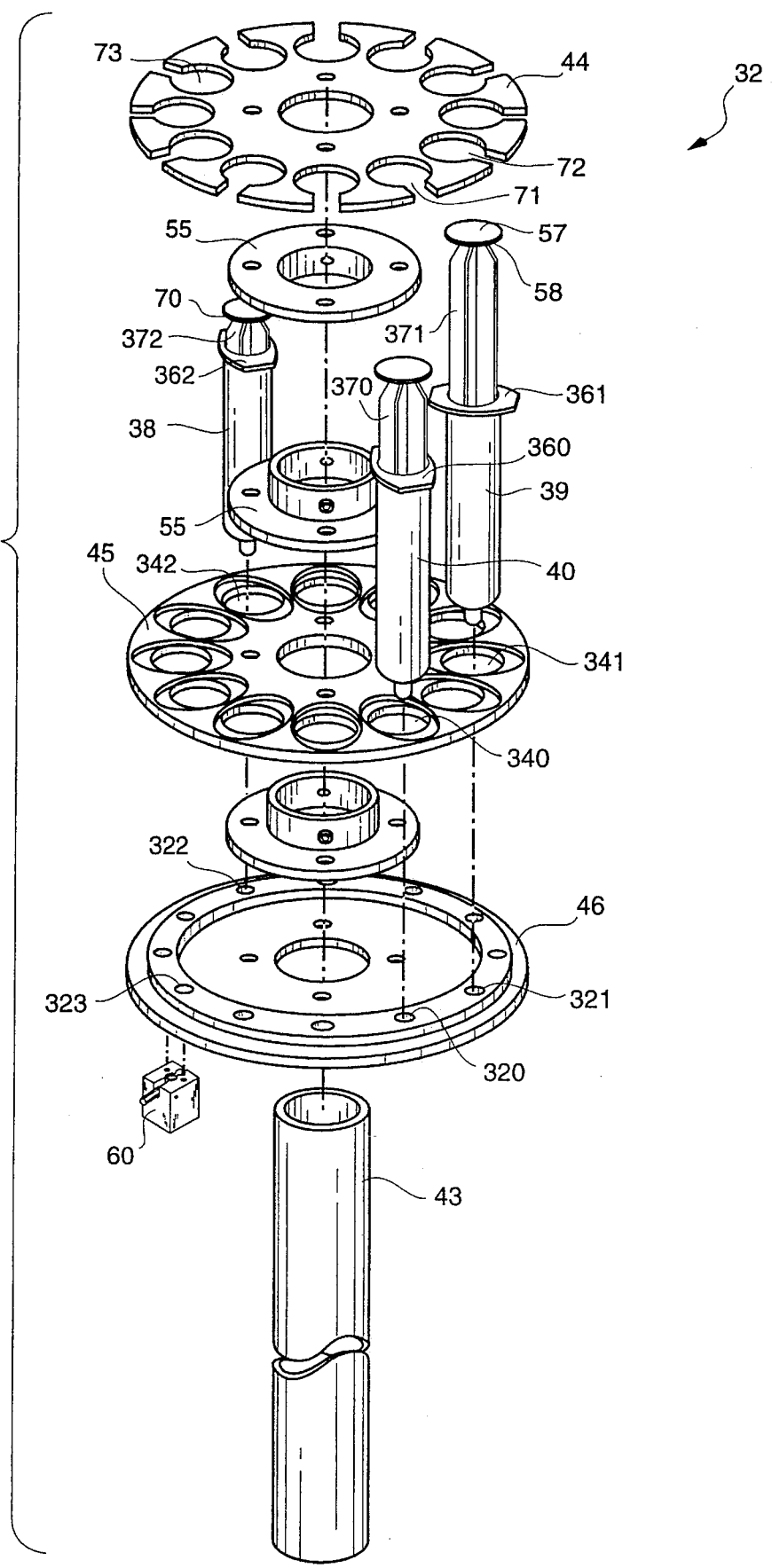
FIG. 3 illustrates the removable cassette/carousel structure for the portable intelligent air sampling system.

The cassette/carousel 32 includes three plates 44-46 interconnected by center support 43, and contains at least one removable and/or disposable syringe 38, and typically multiple disposable syringes as is more easily seen in FIG. 3. In the preferred embodiment, the cassette/carousel 32 contains up to twelve disposable polyethylene or glass syringes each having at or about a 60cc capacity. Larger or smaller volume syringes of varying compositions and/or design may be desirable as a matter of design choice. A syringe in the context of this invention is any container having a plunger mechanism that pulls a sample in when the plunger is withdrawn and pushes a sample out when the plunger is inserted.

Similarly, the cassette/carousel 32 can be designed to accommodate different sizes, types, or numbers of syringes as a matter of design choice. The syringes are removable and/or disposable to prevent contaminating or diluting air samples which may be the case if the syringes were reused in certain applications. However, the syringes need not be replaced in some applications unless they are damaged, contaminated, or badly worn.

In any embodiment, the system can additionally be modified to accommodate solar panels to produce or regenerate power supplies for extended remote use, and an antenna with transmitter/receiver for field communicating. Field communications can be used for numerous purposes including, but not limited to, downloading new programs, transmitting error reports, and transmitting status.

Cassette/carousel 32 is rotatably mountable in housing 10 as illustrated in FIG. 2. The third plate 46 is mounted on drive plate 80 in one orientation guided by at least one key 81, so that the cassette/carousel 32 will fit in only one position relative to drive plate 80 and a "zero position" is always known. Drive plate 80 is opposite drive plate pulley 82 with bearing race 84 therebetween. In the preferred embodiment, bearing race 84 contains a double row of ball bearings 86, although other bearing configurations are optional as a matter of design choice.

Drive plate pulley 82 is rotatable by way of a toothed drive belt 88 attached to carousel motor pulley 90. In the preferred embodiment, carousel motor pulley 90 and drive plate pulley 82 are of equal diameter so that a low power consumption carousel drive motor 92 can incrementally rotate cassette/carousel 32 a stepping motor fashion well known in the art. Ideally, the carousel drive motor 92 produces an output rotation of 0.1° per pulse. Other motor types and/or pulley ratio configurations can be implemented as a matter of design choice.

Precise cassette/carousel 32 rotation indexing and/or zero position status feedback, is provided by interrupt switches 94 and 95 located adjacent to drive plate 80. Interrupt switches 94 and 95 operate independently of each other where interrupt switch 94 identifies the carousel start or "zero" position and interrupt switch 95 identifies each syringe position as the cassette/carousel 32 rotates away from the start position. Knowing the precise syringe locations provides the ability to position a syringe 38 and its inlet/exhaust valve 60, for example, directly over air sample port 98. Interrupt switches 94 and 95 are electrically connected with carousel drive motor 92 and electrical control system 93.

Figure 5:
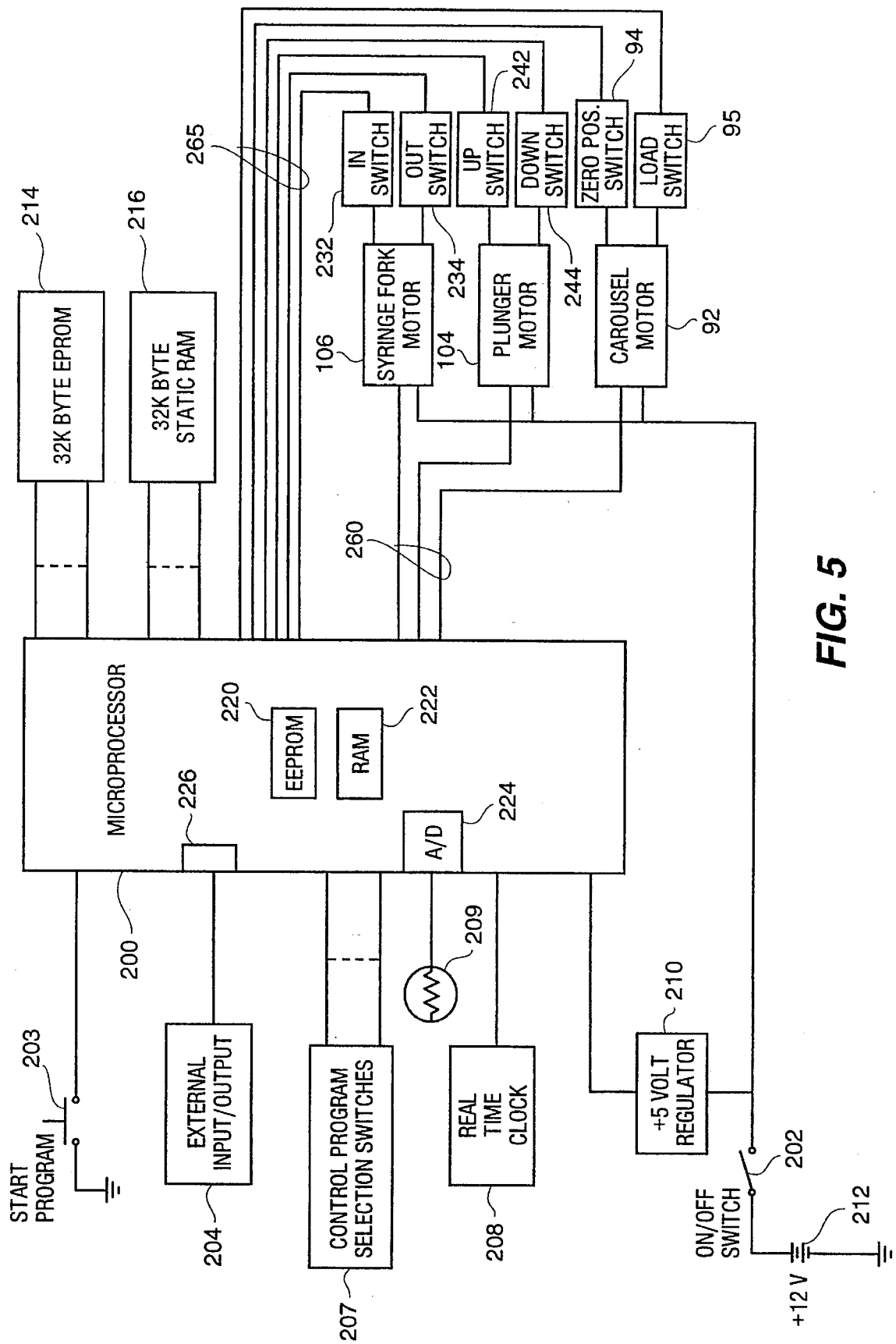
FIG. 5 illustrates a block diagram of the electrical layout for the portable intelligent air sampling system.

Electrical control system 93 controls all system activity as illustrated in FIG. 5 and discussed below. Portable power supply 212 supplies power to system components as illustrated in FIG. 5 and discussed below.

Plunger carriage motor 104 and fork motor 106 are designed to operate in concert under the direction of electrical control systems 93, to withdraw a plunger from a syringe thereby capturing a whole air sample. Fork motor 106 is operable to drive fork block 110 along fork lead screw 108 along plane "A" perpendicular to the action plane of plunger 70 along plane "B," thereby enabling fork 36 to engage the plunger collar 69 of plunger 70 when fork 36 is in its fully extended position. To disengage fork 36 from plunger collar 69, fork motor 106 withdraws fork 36 along plane "A" toward fork motor 106 from position 110B to 110A.

Plunger carriage motor 104 is operable to drive plunger retraction carriage 34 along carriage lead screw 100 in plane "B" parallel to the action of plunger 70. The retraction carriage 34 is attached to fork block 110 and fork motor 106 so that the configuration moves along plane "B" as a single unit guided by hardened slides 101 and 102.

FIG. 2 illustrates the preferred configuration and motor position for plunger carriage motor 104 and fork motor 106. However, plunger carriage motor 104 and fork motor 106 can be alternatively positioned elsewhere within housing 10 for compactness, optimal power output, and/or assembly or maintenance convenience as a matter of design choice.

Lever ramp 402 is positioned to engage valve lever 404 of inlet/exhaust valve 60, or any subsequent valve lever, as carousel 32 is rotated by carousel motor 92 to position any one syringe in the carousel over air sample port 98. The inlet/exhaust valve system is discussed in detail with FIGS. 4A–4C.

Removable Cassette/Carousel—FIGS. 3 and 4A–4C

FIG. 3 illustrates cassette/carousel 32 in an exploded view. The cassette/carousel 32 includes a center support 43 longitudinally disposed within a first plate 44, a second plate 45, and a third plate 46, wherein each plate is substantially equally spaced and axially aligned around the center support 43. The third plate 46 contains syringe ports illustrated by 320–323. Syringes 38–40 are secured between the second plate 45 and the third plate 46 by retaining ring 55 in locations above each respective port below. The syringes are secured by first sliding each in place through any opening as illustrated by 340–342, and second, securing retaining ring 55 over a portion of each syringe collar 360–362 thereby preventing each syringe from being dislodged when each respective plunger 370–372 is withdrawn. Other securing methods may be substituted as a matter of design choice within the scope of the embodiment presently disclosed.

The first plate 44 is positioned an appropriate distance from the second plate 45 so as to prevent any one plunger 370–372 from being pulled completely out of its respective syringe which would otherwise allow the air sample to escape the syringe. A further purpose of the first plate 44 is to protect a withdrawn plunger from accidentally being pushed back into its syringe when the cassette/carousel 32 is being handled by an operator. While the first plate 44 does not make accidental inserting an impossibility, it does significantly reduce the chance, of accidental insertion when cassette/carousel 32 is being handled by an operator. The first platter 44 also contains plunger access slots 71–73, for example, that provides a sample extraction device the limited access needed to press directly down on a withdrawn plunger in order to extract the air sample therein.

As illustrated in FIG. 3, syringe port 323 illustrates the placement of its accompanying inlet/exhaust valve 60. Each syringe port is accompanied by its own inlet/exhaust valve 60 although not shown in FIG. 3 for purposes of figure simplification. In the preferred embodiment, carousel 32 and its three plates 44–46 are configured to accommodate up to 12 syringes, each syringe with its own inlet/exhaust valve, syringe port, syringe opening, and access slot as illustrated in FIG. 3.

FIG. 4A illustrates an exploded view of inlet/exhaust 60. Primary components included in valve 60 include lever 404, valve cylinder 415, and spring 422. Valve cylinder 415 contains a recessed valve tip seat 424 in which elastomer valve tip 416 is contained. Lever 404 contains pivot point 404B through which lever pivot pin 408 passes. Lever 404 distal end 404C traverses valve cylinder 415 between upper valve pin 411 and lower valve pin 412, to rest atop spring tip 423.

Operationally, valve 60 rotates with carousel 32 (not shown) in direction "A." As valve 60 rotates, lever 404 approaches fixed position lever ramp 402 and contacts bevelled edge 402A which engagingly raises lever 404 until lever 404 rests atop the lever ramp 402 in position 402B. As will be more clearly illustrated in FIGS. 4B and 4C, raising lever 404 has a mechanical result of lowering valve cylinder 415 thereby compressing spring 422. Lever ramp 402 position 402B is adjacent to and in line with inlet/exhaust port 98. As the carousel is rotating a syringe into sampling or exhaust position, the system is designed to stop the rotating at a time when valve 60 is directly over air sample port 98, and coincidentally, lever 404 is directly atop lever ramp 402 at surface 402B. In this position, air flutes 430–433 allow a sample to pass into or out of a syringe as further illustrated in FIG. 4C. Lever ramp 402 bevelled surface 402C exists to gradually let lever 404 return to its lowered position, under the pressure of spring 422, without damaging any of the above components.

FIG. 4B illustrates a cross-sectional view of valve 60 when the valve is in a closed position. In the closed position, spring 422 is fully extended thereby pressing against lever 404 at lever point 404C, pivoting at pivot point 404B, so that upward pressure is applied to valve cylinder 415 thereby pressing elastomer valve tip 416 against port opening 420. With elastomer valve tip 416 pressed firmly against port opening 420, air is prevented from passing into or out of syringe 38 at all times when valve 60 is not aligned with air sample port 98 (not shown) or lever ramp 402 surface 402B (not shown). Other features in illustration 4B, that provide an airtight seal between syringe 38 and carousel plate 46, include close tolerances between syringe port 50 and syringe 38, in addition to elastomer seal 418 at the base of syringe port 50.

FIG. 4C illustrates a cross-sectional view of valve 60 when it is in an open position. The open position occurs by lever 404 being raised into the open position by lever ramp 402 surface 402B. When in the open position, valve 60 is positioned directly over inlet/exhaust port 98 which provides an air conduit through housing 10. Lever ramp 402 applies pressure to lever 404, thereby causing valve cylinder 415 with its elastomer valve tip 416 to withdraw from port opening 420. Withdrawing elastomer valve tip 416 from port opening 420, allows air to pass into or out of syringe 38 by way of air flutes 430–433 (shown only in FIG. 4A) and air sampling port 98.

When the carousel rotates valve 60 out of intake/exhaust position, spring 422 pressing against lever 404 distal end 404C, forces valve cylinder 415 and its elastomer valve tip 416 to once again press against port opening 420 thereby sealing the opening. As discussed previously, lever ramp 402, air sample port 98, and housing 10, remain in a fixed position (see FIG. 2) as carousel plate 46 with syringe 38 and valve 60 attached thereto, rotate into and out of sampling and/or exhaust position.

Sampling System Electrical Components–FIG. 5

FIG. 5 illustrates electrical control system 93 in block diagram form. Microprocessor 200 provides the hardware base for controlling the air sampling system. The microprocessor 200 can be a custom design or ready made design microprocessor, provided that the design includes, but does not necessarily need be limited to, components described herein or comparable components. Microprocessor 200 includes an EEPROM 220 having at or about 512 bytes storage capacity, a RAM 222 having at or about 256 bytes storage capacity, and I/O controller 226 having at or about a 16 line capacity and an analog/digital converter 224 having at or about an 8 bit capacity. Additional external EPROM memory 214 and external static RAM memory 216 may also be utilized for larger control program storage and retrieval as a matter of design choice. Alternative components with different specifications may be substituted as a matter of design choice.

The microprocessor 200 has an on/off switch 202 and a +5 V power input provided by a +12 V battery 212 and +5 V stepdown regulator 210. Start program switch 203 provides an interrupt to microprocessor 200 to activate a presently selected and loaded sampling program.

In the preferred embodiment, external input/output source 204 is an RS232 port or other wire dependent port for use in downloading sampling control programs or other information or data to microprocessor 200 by way of I/O controller 226. Alternatively, or in combination with an RS232 port, a wireless communication device may be included in external input/output source 204 as a matter of design choice for ease of downloading in remote locations where wire access is difficult. In either case, external input/output source 204 can function to receive error information or notify operators of problems with a field sampling system, or download parameter programs as needed.

Real-time clock 208 provides an independent monitoring device functioning as an external time reference or event monitor, and an alarm clock feature which allows microprocessor 200 to operationally suspend itself, sleep, or otherwise shut down between sampling periods, thereby conserving power. The period during which the electrical control system 93 is operationally suspended is determined by any combination of fixed and variable time periods. In addition, a fixed or variable time period may include or be determined by the occurrence of an event or the duration of an event based on the real-time clock 208 implemented as a monitoring device. The real-time clock or other monitoring device operates from an independent low voltage battery source in a manner well known in the art and separate from any other power source for the overall system.

Control program selection switch 207 provides a selection of commonly used control programs available for user convenience. By selecting one of the stored control programs, the user can download a new control program without using external input port 204. If no program is downloaded, a default program will be selected automatically. Thermistor 209 utilizes an analog/digital converter port 224 to provide thermal sensing information for evaluation by operators.

Fork motor 106, carriage motor 104, and carousel motor 92 are powered by +12 V battery supply 212. Each motor 104, 106, and 92, independently operate in a closed loop where the respective motor I/O lines 260 and motor interrupt lines 265 interconnect each motor with microprocessor 200. Interrupt switches 232 and 234 drive respective interrupt lines to provide position input to fork motor 106 and microprocessor 200 regarding when fork 36 is fully engaged or disengaged. Interrupt switches 242 and 244 drive respective interrupt lines to provide position input to carriage motor 104 and microprocessor 200, regarding when the carriage is fully extended or withdrawn. Interrupt switches 94 and 95 drive respective interrupt lines to provide position input to carousel motor 92 and microprocessor 200 regarding cassette/carousel 32 position information, in addition to information regarding when a syringe is in the proper position for sampling. Specifically, interrupt switch 94 indicates when the cassette/carousel 32 is in the "zero" or start position. Interrupt switch 95 indicates the location of each successive syringe port on cassette/carousel 32. Where the syringe locations are known, the microprocessor 200 can count the position interrupts from interrupt switch 95 to determine when to shut down carousel motor 92.

Figure 6:
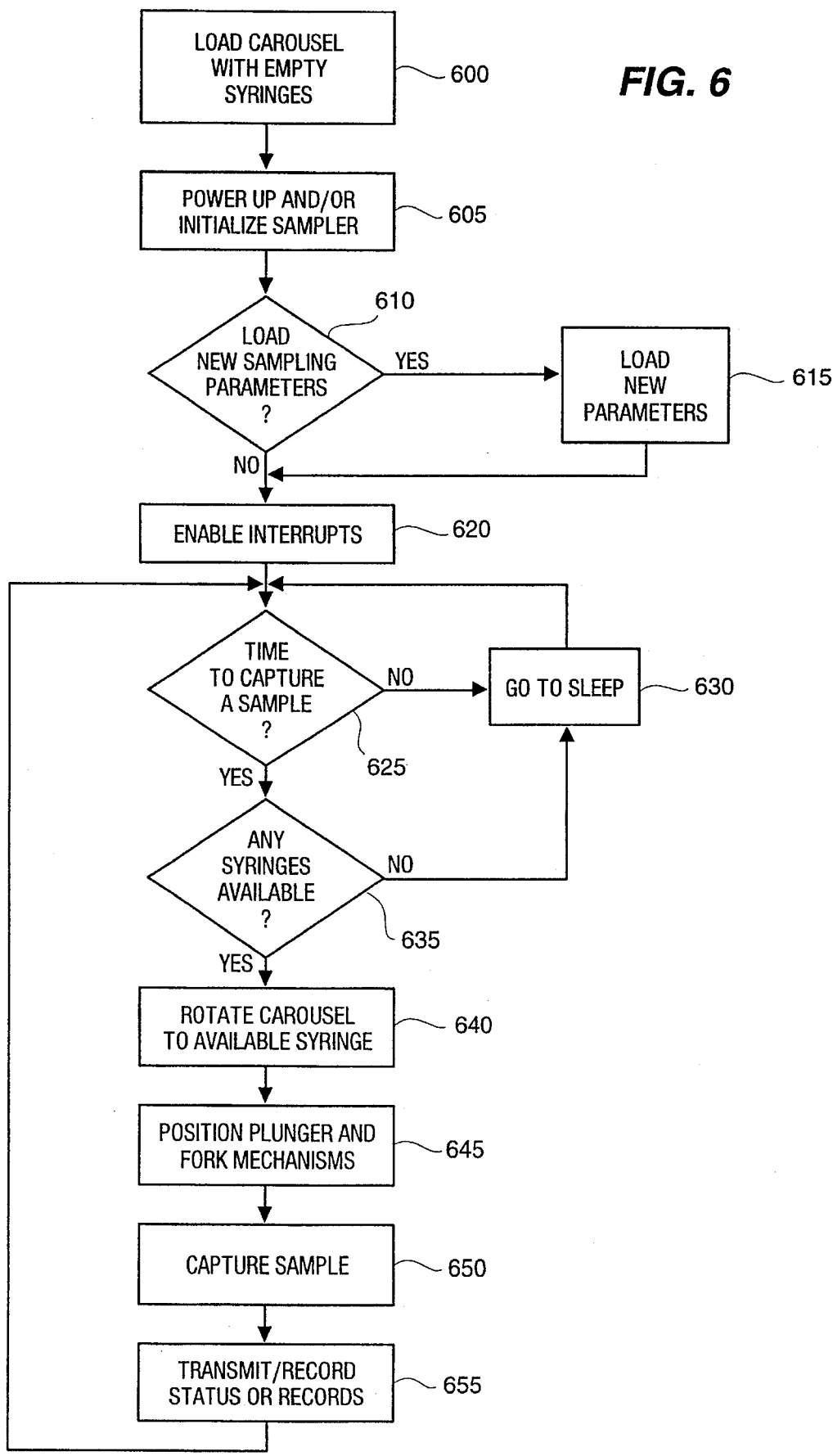
FIG. 6 illustrates a flow diagram of the control system operating steps for capturing a whole air sample.

Sampling Control System Operational Steps—FIG. 6

In operation, capturing a sample begins by loading a carousel containing empty syringes into the sampling device housing at 600. The system is powered up at 605, if not previously powered up, and internal registers, structures, and the real-time clock, are initialized. At 610, if the presently loaded parameters are satisfactory for the present sampling cycle, processing continues by enabling interrupts at 620. If new sampling parameters are desired, new parameters are loaded at 615. New parameters may be loaded by either selecting any one of the pre-loaded select switch parameter sets, downloading a new parameter set from an external source, or accepting default parameters if no parameters are entered. Parameters are loaded into the system in the form of a program.

Once the parameters are selected, processing continues at 620 where interrupts are enabled. With the system functional, processing continues at 625 where the system asks if it is time to capture a sample. If it is not time to capture a sample the system sets a timer and goes to sleep at 630. Until such time as the timer or other event interrupt occurs, the system will shut down all power consuming sources except for the independent battery back up for the timer/event monitor. When it is time to capture a sample, the system wakes up and processing continues at 635 where it is determined if any syringes remain available to take samples. If no syringes are available the system goes to sleep indefinitely at 630. Provided a syringe is available, processing continues at 640 where the carousel is rotated into position to the next available syringe. The syringes are typically in sequential order, however, empty syringe slots may be detected and skipped as necessary. The plunger retraction carriage and fork carriage mechanisms are positioned at 645, so that a sample can be captured at 650.

In operation, the carousel rotation fork and plunger positioning, and sample capturing activity occur as follows. Drive plate 80 rotates cassette/carousel 32 into a position where a syringe, such as syringe 38 in FIG. 2, is aligned over air sample port 98. The start position for plunger retraction carriage 34 is in position 34A adjacent to plunger carriage motor 104. The start position for fork block 110 is in position 110A adjacent to fork motor 106. From the carriage motor 104 and fork motor 106 start positions, fork motor 106 drives fork block 110 along plane "A" toward position 110B so that retraction fork 36 engages plunger collar 69.

Plunger carriage motor 104 then drives plunger retraction carriage 34 along plane "B" toward position 34B for the distance instructed by control system 93. When the desired sample has been taken, fork motor 106 withdraws fork block 110 along plane "A" toward start position 110A and plunger carriage motor 104 withdraws plunger retraction carriage 34 along plane "B" toward start position 34A. Carousel drive motor 92 then rotates cartridge/carousel 32 to the next available syringe and the system awaits instructions from control system 93 to capture the next whole air sample.

As necessary, and as a matter of design choice, an event marker, status indicator, or other error indication, may be recorded and/or transmitted at 655. An event marker may include the time of day, or length of sending time, or other desirable information memorializing a particular sampling event. A status indicator may contain simply successful or unsuccessful indicators for a particular sample. The status indicator may also contain information regarding the status of mechanical or electrical systems in the overall sampling device. Errors may include details of the failure to take a sample as requested, or other system failures that may occur during operation. Any of the above information may be recorded within the sampling device, printed within the sampling device, or transmitted to an external source as a matter of design choice.

Figure 7:
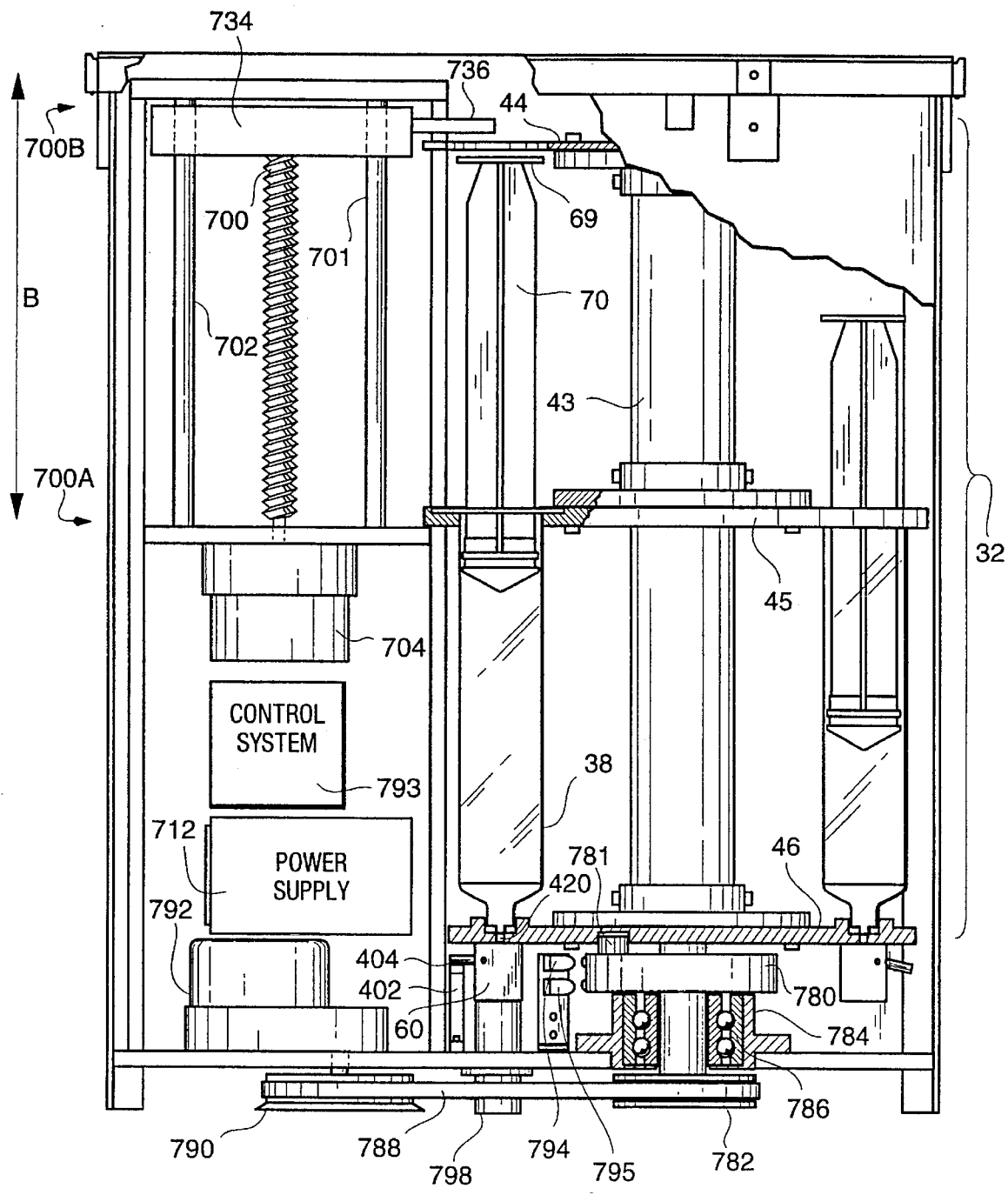
FIG. 7 illustrates internal mechanical components of the sample extraction device.

Sample Extraction System Mechanical Components—FIG. 7

The sample extraction system is substantially the same as the sample capturing system except that the extraction mechanical systems remove samples from each syringe by depressing the syringe plunger. The sample extraction system is a simpler device than the capturing system, although the extraction system would typically be located in a controlled laboratory or field testing environment, or other location where there is access to a gas chromatograph or other analysis system. In operation, a carousel containing samples would be removed from a sample capturing device in the field, and transported to the laboratory where the carousel is inserted in the sample extraction device.

FIG. 7 illustrates the mechanical components of the sample extraction system. As discussed previously, removable carousel 32 with first plate 44, second plate 45, and third plate 36, are all connected by center support 43. All other components are similar to the sample capturing system, including drive plate 780, bearing race 784, ball bearings 786, drive plate key 781, carousel interrupt switches 794 and 795, carousel motor pulley 790, drive plate pulley 782, toothed drive belt 788, and air sample port 798. Electrical control systems 793 are powered by either a battery 712 or other non-portable source as a matter of design choice since portability is less critical in a laboratory environment. Carousel drive motor 792 and plunger motor 704, are powered by the battery 712 or other non-portable source as a matter of design choice. Valve 60, valve lever 404, lever ramp, and syringe port opening 420 all function as described in FIG. 4A–4C.

A fundamental difference between the extraction system and the capturing system, is that the extraction system does not need a fork or fork retraction motor. Plunger depression carriage 734 is driven by carriage screw 700 along dual slides 701 and 702. With plunger 70 in a retracted position as illustrated in FIG. 7, fixed arm 736 extending from plunger depression carriage 734, is designed to pass through the slot openings in first plate 44 (See FIG. 3) located directly above each plunger collar 69, to depressingly engage plunger collar 69 as plunger motor retracts carriage 734 by way of lead screw 700, from position 700B along plane "B" to position 700A. Once the plunger is completely depressed, plunger motor 704 repositions plunger depression carriage 734 back to position 700B so that carousel 32 can rotate a subsequent sample bearing syringe into place under fixed arm 736.

As illustrated in FIG. 4B–4C, each syringe position on carousel plate 46 has an opening 420 through which the sample passes when the syringe plunger is depressed with the valve in an open position. When the plunger of a sample bearing syringe is depressed, the sample escapes through syringe opening 50 and cylinder 415 flutes 430–433, out air sample port 98 and into a gas chromatography device (not shown) or other testing device as desired without contamination or other transferring processes.

Figure 8:
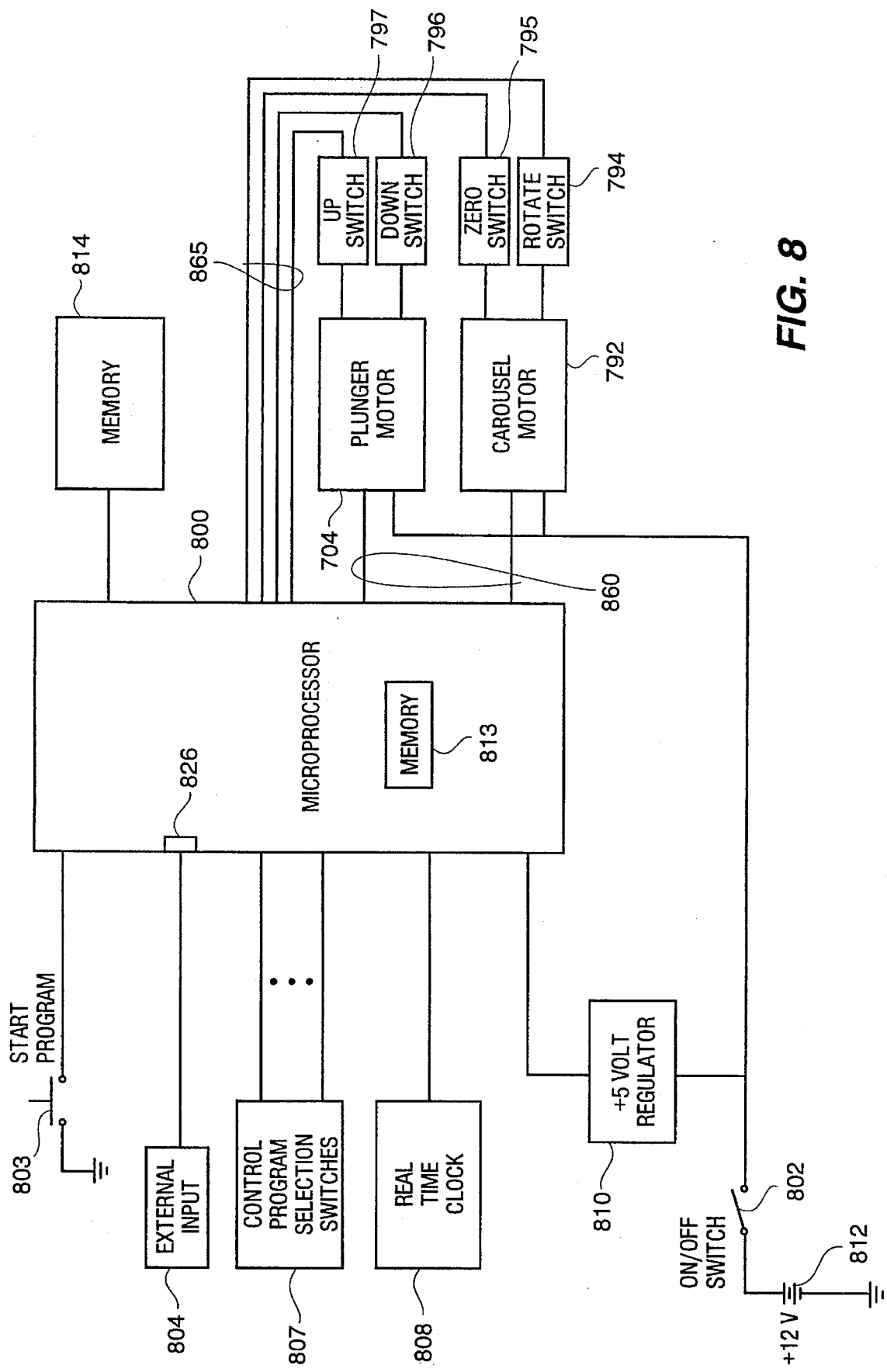
FIG. 8 illustrates a block diagram of the electrical layout for the sample extraction device.

Sample Extraction Electrical Systems—FIG. 8

FIG. 8 illustrates the FIG. 7 electrical control system 793, in block diagram form. Micro-processor 800 provides the hardware base for controlling the sample extraction system. The micro-processor 800 has an on/off switch 802 which carries +12 V power 812 to a +5 V stepdown regulator 810. The remaining +12 V power is directed to carousel motor 792 and plunger motor 704. The start program switch 803 is either manually or remotely invoked to activate the presently selected extraction program and parameters.

In the preferred embodiment, external input 804 is an RS232 port or other wire or wireless port for downloading sample control programs or other information or data to micro-processor 800 by way of IO controller 826. The external input may also include status or event marker information useful in determining sampling order and quantity, or other information useful in extracting samples. Where external information is not useful when extracting the samples, pre-loaded extraction control programs may be selected by selection switches 807. If no downloading or preselected program is required, a default program will be entered. Where it is desirable to extract a sample over a period of time, or where other timing critical extraction conditions exist, real-time clock and alarm timer 808 is available to send an alarm interrupt to micro-processor 800 so that a subsequent sample can be extracted based on a time interval, time of day, or the occurrence of some other event. Memory 813 and 814 is available for recording information or downloaded programs as needed.

Motors 792 and 704 operate independently in respective closed feedback loops within microprocessor 800 by way of motor I/O lines 860 and motor interrupt lines 865. Zero switch 795 and rotate switch 794, assist carousel motor 792 in determining the first syringe position in carousel 32, and subsequent syringe positions respectively. Up switch 797 and down switch 796, assist plunger motor 704 in determining when plunger depression carriage 734 is fully extended or retracted.

Figure 9:
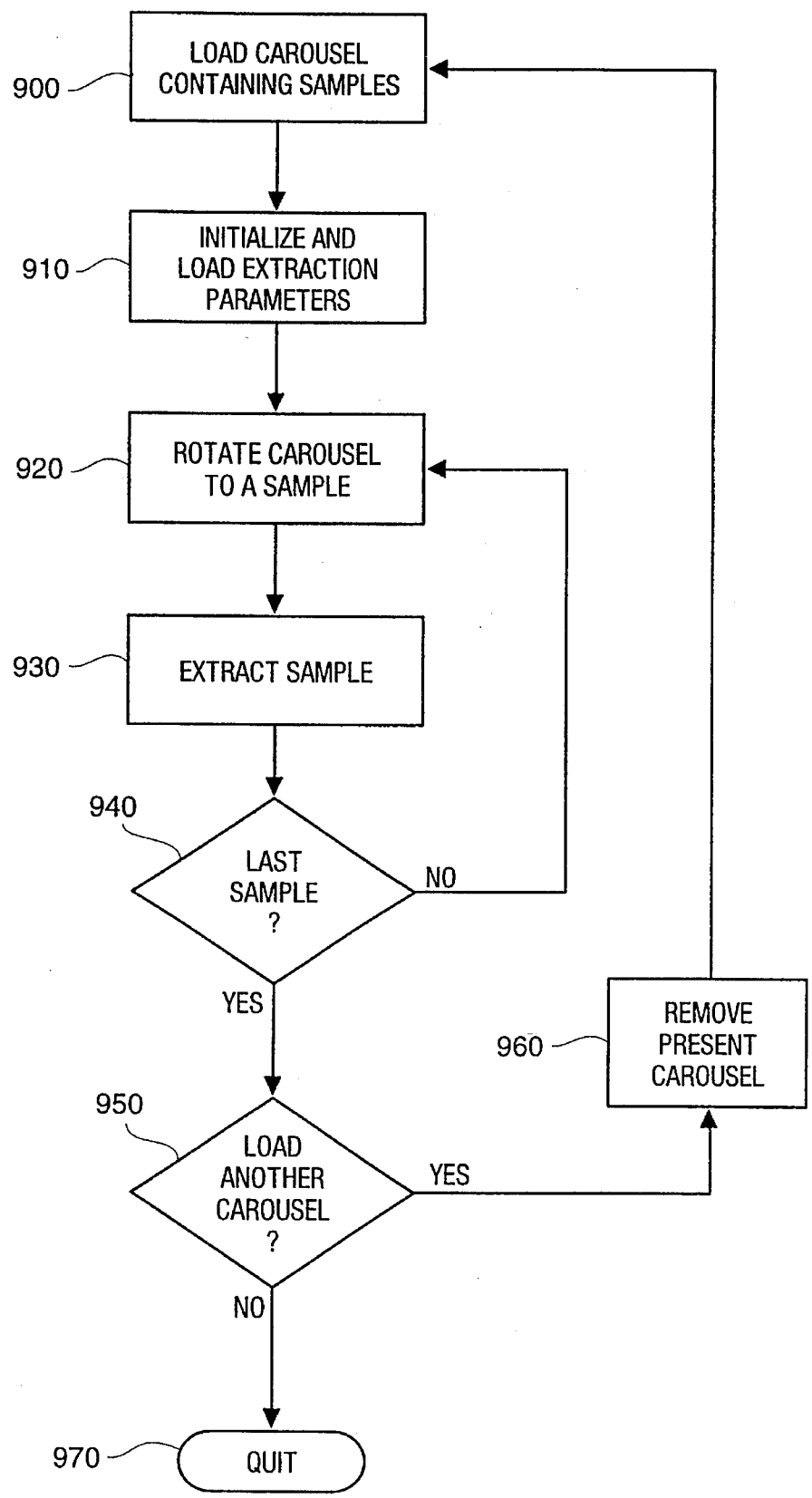
FIG. 9 illustrates a flow diagram of the control system operating steps for extracting a whole air sample.

Sample Extraction System Operational Steps—FIG. 9

A carousel containing samples is loaded into the extraction system at step 900. Extraction parameters are loaded and the system initialized at step 910. The program parameter may be loaded from an external source, selected from among a number of pre-loaded programs, or a default parameter set loaded if no other parameters are provided. A sample is rotated into position at step 920, and the sample extracted at step 930, as discussed previously. If at step 940 there are subsequent samples to extract, processing continues at step 920. Sleep timer functions as discussed in FIG. 6 step 630, can be implemented in the extraction operational steps of FIG. 9 as a matter of design choice. If a subsequent carousel is available for testing at step 950, the present removable carousel is removed at step 960 and a new sample bearing carousel inserted at step 900. If no additional carousels are available for testing at step 950 processing quits at step 970.

Summary

The portable intelligent whole air sampling system provides a sample capturing device and sample extraction device with a removable carousel for transporting samples therebetween. While specific embodiments of this invention are disclosed herein, it is expected that those skilled in the art can and will design alternate embodiments that fall within the scope of the following claims.

We claim:

1. An air sampling system comprising:
   means for removably affixing a plurality of sample containers in a removable carousel within a housing;
   means for controlling said air sampling system from within said housing according to at least one programmable sampling parameter selected from the group consisting of: flow rate, time of day, time period, occurrence of an event, and total volume, independently for each one of said plurality of sample containers; and means, responsive to said controlling means, for variably capturing a whole air sample in a precise amount that can be less than an entire sample container volume for any of said plurality of sample containers by way of an air sample port through said housing.

2. An air sampling system according to claim 1 including:

means for sealing said housing to protect said air sampling system from external elements.

3. An air sampling system according to claim 1 wherein said means for removably affixing includes:

means for mounting said removable carousel in said housing, said removable carousel having a plurality of removable syringes therein.

4. An air sampling system according to claim 1 wherein said means for controlling includes:

means for individually manipulating each of said plurality of sample containers with at least one motor common to all of said plurality of sample containers; and means for transferring said whole air sample into and out of each of said plurality of sample containers by way of a resealable valve, wherein said resealable valve prevents said whole air sample from unintentionally escaping any one of said plurality of sample containers once said whole air sample has been captured therein.

5. An air sampling system according to claim 1, wherein said means for controlling includes:

means for powering said air sampling system in at least one portable form selected from the group consisting of: battery, solar conversion, generator.

6. An air sampling system according to claim 5 further including:

means for operationally suspending said control means for at least one period selected from the group consisting of: a fixed period, and a variable period; and means, responsive to said at least one period ending, for generating an interrupt from a monitoring device within said housing to awaken said control means, said monitoring device being powered independently from any other power source for said air sampling system.

7. An air sampling system according to claim 1 further including:

means for communicating said at least one programmable sampling parameter to said air sampling system from a location external to said air sampling system.

8. An air sampling system according to claim 7 wherein said means for communicating includes:

means for transmitting between said air sampling system and said location external to said air sampling system by way of a medium selected from the group consisting of: electrical wire medium and wireless medium, wherein a transmission is of at least one type selected from the group consisting of: error information, parameter program downloading, event markers, and status information.

9. An air sampling system according to claim 1 further including:

means for communicating said at least one programmable sampling parameter into said air sampling system from a source internal to said air sampling system.

10. An air sampling system according to claim 9 wherein said means for communicating includes:

means for selecting from a plurality of predefined programmable sampling parameters stored within said air sampling system in at least one manner selected from the group consisting of: predefined, default, and user selection.

11. An air sampling system according to claim 1 wherein said means for capturing includes:

means for selecting an available container from said plurality of sample containers, wherein said available container is a syringe having a plunger therein;

means for withdrawing said plunger from within said available container thereby drawing in said whole air sample by way of said air sample port; and means for sealing said available container to prevent said whole air sample from unintentionally escaping.

12. An air sampling system according to claim 1, further including:

means for removing said carousel containing said plurality of sample containers from said housing and placing said carousel in a sample extracting device;

means for extracting said whole air sample from at least one of said plurality of sample containers by way of said air sample port; and means for controlling said sample extracting device from within said extracting device according to at least one sampling parameter selected from the group consisting of: flow rate, user input command, time period, time of day, occurrence of an event, and total volume extracted, for each of said at least one said plurality of sampling containers.

13. A method for air sampling comprising:

removably affixing a plurality of sample containers in a removable carousel within a housing;

controlling said air sampling system from within said housing according to at least one programmable sampling parameter selected from the group consisting of: flow rate, time of day, time period, occurrence of an event, and total volume, independently for each one of said plurality of sample containers; and variably capturing a whole air sample in a precise amount that can be less than an entire sample container volume for any of said plurality of sample containers by way of an air sample port through said housing, in response to said step of controlling.

14. A method according to claim 13 including:

sealing said housing to protect said air sampling system from external elements.

15. A method according to claim 13 wherein said removably affixing step includes:

mounting said removable carousel in said housing, said removable carousel having a plurality of removable syringes therein.

16. A method according to claim 13 wherein said controlling step includes:

individually manipulating each of said plurality of sample containers with at least one motor common to all of said plurality of sample containers; and transferring said whole air sample into and out of each of said plurality of sample containers by way of a resealable valve, wherein said resealable valve prevents said whole air sample from unintentionally escaping any one of said plurality of sample containers once said whole air sample has been captured therein.

17. A method according to claim 13, wherein said controlling step includes:

powering said air sampling system in at least one portable form selected from the group consisting of: battery, solar conversion, and generator.

18. A method according to claim 17 further including:

operationally suspending said controlling step for at least one period selected from the group consisting of: a fixed period, and a variable period; and generating an interrupt from a monitoring device within said housing to awaken said controlling step in response to said at least one period ending, said monitoring device being powered independently from any other power source for said air sampling system.

19. A method according to claim 13 further including:

communicating said at least one programmable sampling parameter to said air sampling system from a location external to said air sampling system.

20. A method according to claim 19 wherein said communicating step includes:

transmitting between said air sampling system and said location external to said air sampling system by way of a medium selected from the group consisting of: electrical wire medium and wireless medium, wherein a transmission is of at least one type selected from the group consisting of: error information, parameter program downloading, event markers, and status information.

21. A method according to claim 13 further including:

communicating said at least one programmable sampling parameter into said air sampling system from a source internal to said air sampling system.

22. A method according to claim 21 wherein said communicating step includes:

selecting from a plurality of predefined programmable sampling parameters stored within said air sampling system in at least one manner selected from the group consisting of: predefined, default, and user selection.

23. A method according to claim 13 wherein said capturing step includes:

selecting an available container from said plurality of sample containers, wherein said available container is a syringe having a plunger therein;

withdrawing said plunger from within said available container thereby drawing in said whole air sample by way of said air sample port; and sealing said available container to prevent said whole air sample from unintentionally escaping.

24. A method according to claim 13, further including:

removing said carousel containing said plurality of sample containers from said housing and placing said carousel in a sample extracting device;

extracting said whole air sample from at least one of said plurality of sample containers by way of said air sample port; and controlling said sample extracting device from within said extracting device according to at least one sampling parameter selected from the group consisting of: flow rate, user input command, time period, time of day, occurrence of an event, and total volume extracted, for each of said at least one said plurality of sampling containers.

* * * * *